United States Patent [19]

Webb

[11] Patent Number: 4,763,644
[45] Date of Patent: Aug. 16, 1988

[54] SPINAL FIXATION

[76] Inventor: Peter J. Webb, 134 Harley St., London W1, United Kingdom

[21] Appl. No.: 843,561

[22] Filed: Mar. 25, 1986

[51] Int. Cl.$^4$ .............................................. A61B 17/56
[52] U.S. Cl. ........................................ 128/69; 128/78
[58] Field of Search .................. 128/68, 69, 92 B, 78, 128/92 D, 92 E

[56] References Cited

U.S. PATENT DOCUMENTS

| 4,047,523 | 1/1987 | Hall | 128/69 |
| 4,611,581 | 1/1987 | Steffee | 128/69 |
| 4,648,388 | 3/1987 | Steffee | 128/69 |
| 4,653,481 | 3/1987 | Howland et al. | 128/69 |

FOREIGN PATENT DOCUMENTS

| 1241292 | 8/1971 | United Kingdom . |
| 2051581 | 1/1981 | United Kingdom . |
| 2131300 | 6/1984 | United Kingdom . |

OTHER PUBLICATIONS

EPO Publication 0 128058 A1, published Dec. 12, 1984, Inventor: Cotrel.
EPO Publication 0 140 790 A2, published May 8, 1985, Inventor: William Peze.
U.K. Patent Application 2 131 300 A, published June 20, 1984 for Spinal Compression/Distraction Hooks, Inventor:*.

Primary Examiner—Paul T. Sewell
Assistant Examiner—Huong Q. Pham
Attorney, Agent, or Firm—Hall, Myers & Rose

[57] ABSTRACT

A spinal scoliosis fixation implant comprises a plurality of devices which are associated with respective vertebrae and which are interconnected by a single semi-rigid wire, or by a cable with abutment ferrules. Each device may comprise a bone screw or hook with a slotted, externally threaded head into which is inserted the wire or cable and thereon a clamping element which projects slightly from the mouth of the slot, and a nut which is screwed onto the head to press the clamping element onto the wire or cable. The wire or cable can be unclamped, to permit adjustment of the device along the wire or cable, by simply untightening the nut.

2 Claims, 2 Drawing Sheets

SPINAL FIXATION

BACKGROUND OF THE INVENTION

1. Field of the Invention

This invention relates to spinal fixation.

2. Description of the Prior Art

The normal human spine is a segmented column of vertebrae, coupled together by intervertebral joints of two types; viz. anteriorly by intervertebral discs and posteriorly by zygoapophyseal gliding synovial joints.

Spinal deformity occurs when the normal alignment of the vertebrae is upset or disturbed by altered muscle or nerve function or, more rarely, by abnormal bony structure. Once deformity has been established, secondary changes take place which maintain the abnormality and prevent its return to normal. When the deformity is sufficiently profound, it may be associated with an instability such that the deformity will tend to increase with the axial loading by gravity in spite of the removal of the causative factor.

Under these circumstances it is often necessary to fix together the vertebral levels, after having returned them towards their normal position if safely possible. For this purpose, it is known from, for example British Patent Specification Nos. 1241292; 2051581 and 2131300; U.S. Pat. No. 4,611,581 and European Patent Specification No. 0128058, to provide fixation implants, each of which comprises an elongate member and a plurality of devices for anchoring the elongate member to respective vertebrae. British Patent Specification No. 1241292 discloses an implant which is for use posteriorly and in which the elongate member is a rigid channel member formed at intervals therealong with bores for receiving respective bone hooks having threaded shanks for insertion through the bores to cooperate with nuts which urge the vertebrae towards the channel member. This system has a number of disadvantages, for example that the hooks, and thus their vertebrae, cannot be adjusted relative to each other along the member after fixation and that the hooks cannot be adjusted around the member. The implant disclosed in U.S. Pat. No. 4,611,581 has similar disadvantages, except that adjustment of its bone screws, and thus their vertebrae, relative to each other along the member after fixation is possible, but to an extent limited by bridging portions among slots along the plate-form elongate member. Another implant, shown in FIG. 1 of British Patent Specification No. 2051581, is for use posteriorly and comprises as its elongate member a rigid rod having two hook-like devices connected to respective ends thereof which hook respectively over and under respective vertebrae. With the implant in position on the spine, the devices are adjustable only away from each other. Another of these implants, also shown in that Specification, is again for use posteriorly and comprises as its elongate member a rigid screw-threaded rod having hook-like devices connected thereto which hook respectively over and under respective vertebrae. Each device includes a channel-form base portion which receives the threaded rod and the channel of which incorporates a bore which houses a sleeve encircling the rod. The external diameter of the sleeve is greater than the width of the mouth of the channel, so that the sleeve and thus the rod cannot be displaced radially out of the channel. However, the sleeve can be removed longitudinally from the channel in one direction only, whereafter the rod can be removed radially out of the channel. A nut threaded onto the rod prevents the device from sliding in one direction along the rod and simultaneously obturates the outer end of the bore to prevent the sleeve from leaving the bore, provided that the device is adjacent the nut. This implant has the disadvantage that removal of a nut from among the nuts on the rod involves the disconnection of the hook-like devices between that nut and one end of the rod, as does insertion of an extra nut among the nuts on the rod. Moreover, the need to thread the nut along the rod results in the device being rather slow to assemble and can result in damage to soft tissue if carried out in situ. Another disadvantage is that, with the apparatus in situ, the hook part is not fixed by the apparatus against rotation about the rod and is fixed by the apparatus against movement along the rod in one direction only. Another known implant, but which is for use anteriorly, comprises a cable and several devices which are fixable in a substantially permanent manner to the cable at intervals therealong. These devices resemble bone screws in order that they may be able to be screwed into respective vertebrae. A third known implant, also for use anteriorly only, comprises a threaded rod, whilst its bone-screw-like devices incorporate rotatable nuts receiving the threaded rod and adjustable therealong by rotation, in order to allow in situ adjustment of the vertebral levels towards and away from each other.

Described with reference to FIG. 8, for example, of European Patent Specification No. 0128058 is a hook-like device consisting of three separate parts, namely a hook part provided with a U-shaped channel for receiving a rod; a sleeve part formed with a conical external surface arranged to be pressed into a correspondingly shaped internal surface of the channel from one end of the channel to grip the rod by a wedge effect, the sleeve part carrying a set screw for clamping the sleeve part to the rod and also including teeth for engaging in stabilization notches in the said one end of the channel; and a ring part arranged to abut the other end of the channel, carrying a set screw for clamping the ring part to the rod and also including teeth for engaging in stabilization notches in the other end of the channel. Not only is this apparatus somewhat complicated to assemble, with the added difficulty that the surgeon has to ensure for each device that the wedge effect, the tightening of both set screws and the engaging of both sets of teeth in their notches have all been correctly achieved, but, if with the apparatus in situ, he decides to add or remove a device at a particular vertebra, all of the other devices between that vertebra and the nearer end of the rod have to be dismantled to permit addition or removal of the device.

SUMMARY OF THE INVENTION

According to one aspect of the present invention, there is provided a device for use in spinal fixation, comprising anchoring means whereby said device is anchored to a vertebra, and fixing means whereby said device is readily releasably fixed to an elongate member, said fixing means comprising first and second clamping elements which bear against respective transversely opposite sides of said elongate member and thereby clamp the elongate member between them, and readily releasable means which urges the clamping elements towards each other, said first clamping element being formed with a channel-shaped slot for receiving said elongate member.

According to another aspect of the present invention, there is provided a device for use in spinal fixation, comprising anchoring means whereby said device is anchored to a vertebra, and fixing means whereby said device is readily releasably fixed to an elongate member, said fixing means comprising a part formed with a channel-shaped slot for receiving said elongate member, said fixing means comprising a part formed with a channel-shaped slot for receiving said elongate member, and a readily releasable clamping element arranged to apply a force to one of two transversely opposite sides of said elongate member and thereby to cause the other of said two transversely opposite sides of said elongate member to bear against said part to clamp said elongate member relative to said part.

Owing to the present invention, not only can the implant be relatively quickly assembled and the anchoring means, such as a hook or bone screw, be so fixed to the member as to oppose rotation thereof relative to the member and movement thereof along the member in both directions, but also the addition or removal of a device in situ need not involve dismantling of others of the devices, and yet the positioning of the devices along the elongate member need nowhere be limited by the elongate member itself.

BRIEF DESCRIPTION OF THE DRAWINGS

In order that the invention may be clearly understood and readily carried into effect, reference will now be made, by way of example, to the accompanying drawings, in which.

DESCRIPTION OF THE PREFERRED EMBODIMENTS

Figure 1:
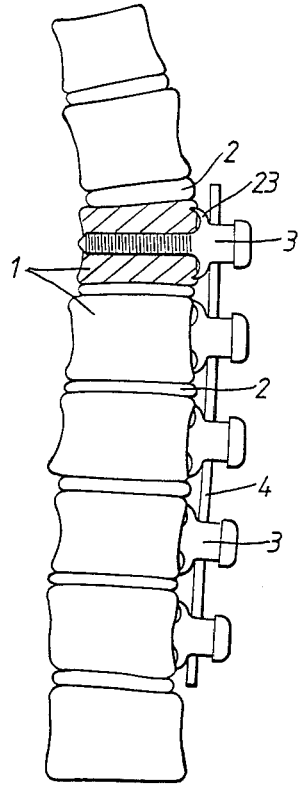
FIG. 1 shows a lateral elevation of a spinal scoliosis fixation implant in situ on a spine.

Referring to FIG. 1, the spine comprises a plurality of vertebrae 1 with discs 2 therebetween. Associated with the respective vertebrae are devices 3 which are interconnected by a single wire 4 which may be about ⅛ inch diameter and which is semi-rigid.

Figure 2:
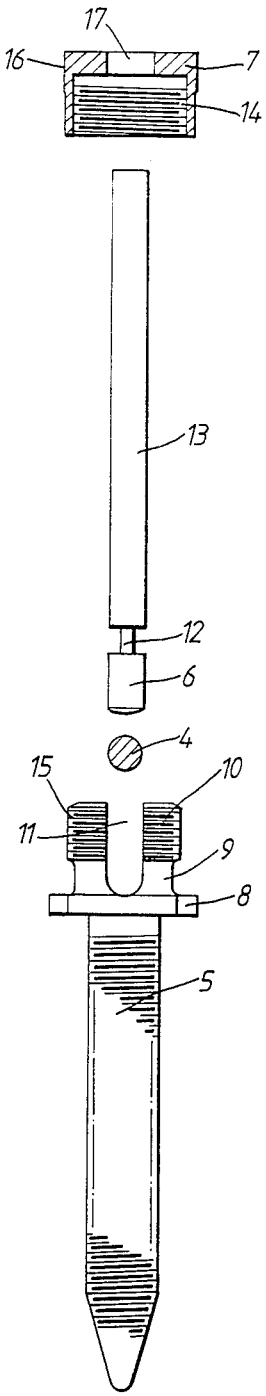
FIG. 2 shows an exploded, sectional, plan view of one of at least three identical devices of the implant.

Referring to FIG. 2, each device 3, comprises at least three components, one being a bone screw 5, the second being a clamping element 6 and the third a cap-form nut 7. The shank of the screw 5 constitutes anchoring means, and the head of the screw 5 constitutes another clamping element which, with the element 6, constitutes fixing means for the wire 4. The screw 5 has its head consisting of a substantially rectangular flange 8, a plain neck 9, and an externally threaded head 10. A slot 11 extends diametrally through the parts 9 and 10. The wire 4 almost fills that portion of the slot 11 formed in the neck 9. The clamping element 6 is received in that portion of the slot 11 formed in the head 10 and projects slightly out of the mouth of the slot in the assembled condition of the device. The element 6 is connected by a very thin neck 12 to a rod 13 which can be gripped between the thumb and forefinger of the surgeon. The nut 7 constitutes readily releasable means and is internally screwthreaded at 14 to co-operate with the external screwthreading 15 of the head 10. The nut 7 is moreover formed with an hexagonal external surface 16 and with a central bore 17 through which the rod 13 can be passed, but not the element 6.

For the purpose of implantation, the screws 5 are introduced into the vertebral bodies by an appropriately shaped screwdriver, the slots 11 being finally aligned with one another so that the wire 4 can be introduced into all of them by being simply laid in them. The elements 6 are then introduced into the slots 11 the surgeon positioning them using the rod 13, and the nuts 7 screwed down, their top walls coming into contact with the elements 6, until the wire 4 is retained with slightly looseness in the screws 5. Thereupon, the positions of the screws relative to each other along the wire 4 and thus the positions of the vertebral bodies relative to each other along the spine can be adjusted as desired towards or away from each other, as the need for spinal correction determines. The nuts 7 can then be tightened to a predetermined torque, forcing the elements 6 to clamp the wire 4 against the screws 5, to prevent slippage of the screws 5 relative to the wire 4 then the rods 13 can be broken off at the necks 12.

The vertebrae are thereby held safely in the desired position and maintained there until an induced arthrodesis has taken place.

If, for some reason, subsequent correction of the positions of the screws 5 along the wire 4 is required, then the nuts 7 are readily untightened to allow such adjustment, which is a simple linear sliding movement.

Figure 5:
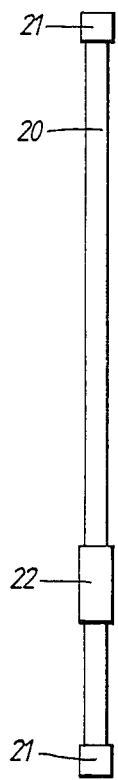
FIG. 5 shows a lateral elevation of a modified version of an elongate member of the implant.

In certain cases where the curvature of the spine is too great to permit use of a semi-rigid wire, in place of the wire 4 there can instead be employed, as shown in FIG. 5, a flexible cable 20, which is provided at its respective ends with fixed ferrules 21 each of an external diameter greater than the width of the slots 11. The cable 20 also carries a sliding ferrule 22 also of an external diameter greater than the width of the slots 11.

In implantation, the lower ferrule 21, say, is brought into abutment against the head 10 of the lowest device 3. After clamping of the cable 20 to the devices 3, and with the ferrule 22 immediately above the uppermost device 3, the ferrule 22 and the cable 20 are transversely severed, such severing coincidentally clamping the lower piece of the ferrule 22 to the cable 20 to deter subsequent fraying of the upper cable end.

If desired, there can be employed with the screws 5 respective toothed washers 23, as shown in FIG. 1, which engage in the bone of the vertebral bodies.

Figure 3:
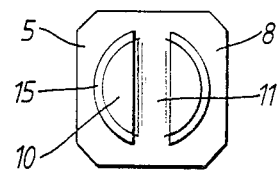
FIG. 3 shows an anterior elevation of a bone screw included in the device.
Figure 4:
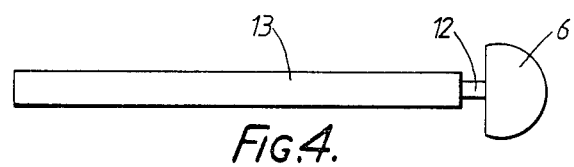
FIG. 4 shows a lateral elevation of another element of the device.

The apparatus shown in FIGS. 1 to 4 can be used posteriorly, but with devices being identical to that shown in FIGS. 2 to 4, except that the shanks of the screws 5 are replaced by hooks hooked about the posterior elements of the vertebrae, either the laminae or transverse processes, so that the hook-like devices in this case can be adjusted towards and away from each other along a wire.

I claim:

1. A device for use in spinal fixation, comprising:
an elongate member, anchoring means for securing said device to a vertebra, and fixing means whereby said device is readily releasably fixed to said elongate member, said fixing means comprising first and second clamping elements which bear against respective transversely opposite sides of said elongate member and thereby clamp the elongate member between them, and readily releasable means which urges the clamping elements towards each other, said first clamping element being formed with a channel-shaped slot for receiving said elongate member, said slot having a mouth, said second clamping element projecting slightly out of the mouth of the slot in an assembled condition of the device, and said readily releasable means comprising a nut screwed onto said first clamping element to press said second clamping element against said elongate member.

2. A device for use in spinal fixation, comprising: an elongate member, anchoring means for securing said device to a vertebra, and fixing means whereby said device is readily releasably fixed to said elongate member, said fixing means comprising first and second clamping elements which bear against respective transversely opposite sides of said elongate member and thereby clamp the elongate member between them, and readily releasable means which urges the clamping elements towards each other, said first clamping element being formed with a channel-slot for receiving said elongate member, said channel slot having a base, said second clamping element being connected by a very thin neck to a rod which extends away from the base of the slot.

* * * * *